(12) United States Patent
Fergason

(10) Patent No.: US 7,550,698 B2
(45) Date of Patent: Jun. 23, 2009

(54) LIGHT SENSOR ARRANGEMENT FOR AUTO-DARKENING LENSES AND METHOD

(75) Inventor: John D. Fergason, Cupertino, CA (US)

(73) Assignee: Lightswitch Safety Systems, Inc., Mountain View, CA (US)

( * ) Notice: Subject to any disclaimer, the term of this patent is extended or adjusted under 35 U.S.C. 154(b) by 95 days.

(21) Appl. No.: 10/888,197

(22) Filed: Jul. 9, 2004

(65) Prior Publication Data

US 2005/0007667 A1    Jan. 13, 2005

Related U.S. Application Data

(60) Provisional application No. 60/486,091, filed on Jul. 10, 2003.

(51) Int. Cl.
*G01J 1/20* (2006.01)

(52) U.S. Cl. ..................... 250/201.1; 359/601

(58) Field of Classification Search ........... 250/221, 250/205, 216, 226, 201.1, 206; 359/601
See application file for complete search history.

(56) References Cited

U.S. PATENT DOCUMENTS

| | | |
|---|---|---|
| 3,731,986 A | 5/1973 | Fergason |
| 3,881,809 A | 5/1975 | Fergason et al. |
| 4,039,254 A | 8/1977 | Harsch |
| 4,039,803 A * | 8/1977 | Harsch ............... 219/147 |
| RE29,684 E * | 6/1978 | Gordon ............... 219/147 |
| 4,385,806 A | 5/1983 | Fergason |
| 4,436,376 A | 3/1984 | Fergason |
| 4,540,243 A | 9/1985 | Fergason |
| 4,582,396 A | 4/1986 | Bos et al. |
| RE32,521 E | 10/1987 | Fergason |
| 5,074,647 A | 12/1991 | Fergason et al. |
| 5,208,688 A | 5/1993 | Fergason et al. |
| 5,248,880 A | 9/1993 | Fergason |

(Continued)

FOREIGN PATENT DOCUMENTS

DE    24 42 998    3/1976

(Continued)

OTHER PUBLICATIONS

International Search Report relating to application PCT/US2004/021872, dated mailed Dec. 3, 2004.

*Primary Examiner*—Georgia Y Epps
*Assistant Examiner*—Kevin Wyatt
(74) *Attorney, Agent, or Firm*—Renner, Otto, Boiselle & Sklar, LLP

(57) ABSTRACT

A control for an auto-darkening lens or other optical device monitors light incident on the viewing area or in relatively close proximity to the viewing area of the lens to provide accurate light sensing and to avoid inadvertent blocking of light to one or more light sensors. Reflectors, prisms, prism strips and the like may be used to direct light to the sensor(s). A method for detecting light incident on an auto-darkening lens and a method for controlling an auto-darkening lens direct light from the viewing area of an auto-darkening lens or from relatively close proximity to the viewing area to one or more sensors to detect such light and, accordingly, to control operation of the auto-darkening lens.

35 Claims, 8 Drawing Sheets

U.S. PATENT DOCUMENTS

| | | | |
|---|---|---|---|
| 5,252,817 A | 10/1993 | Fergason et al. | |
| 5,254,852 A * | 10/1993 | Filipovich et al. | 250/214 VT |
| 5,347,383 A | 9/1994 | Fergason | |
| 5,434,407 A * | 7/1995 | Bauer et al. | 250/227.24 |
| 5,444,232 A * | 8/1995 | Gunz et al. | 250/201.1 |
| 5,510,609 A | 4/1996 | Ackermann | |
| 5,519,122 A | 5/1996 | Ajito et al. | |
| 5,519,522 A | 5/1996 | Fergason | |
| 5,608,567 A | 3/1997 | Grupp | |
| 5,959,705 A * | 9/1999 | Fergason | 349/14 |
| 6,053,936 A * | 4/2000 | Koyama et al. | 607/88 |
| 6,067,129 A | 5/2000 | Fergason | |
| 6,204,974 B1 | 3/2001 | Spitzer | |
| 6,242,711 B1 | 6/2001 | Cooper | |
| 6,244,703 B1 * | 6/2001 | Resnikoff et al. | 351/44 |
| 6,369,952 B1 | 4/2002 | Rallison et al. | |
| 6,384,982 B1 * | 5/2002 | Spitzer | 359/630 |
| 6,504,658 B1 * | 1/2003 | Bignolles et al. | 359/728 |
| 6,755,542 B2 * | 6/2004 | Bechtel et al. | 359/601 |
| 2002/0097496 A1 * | 7/2002 | Lu | 359/628 |
| 2002/0140899 A1 * | 10/2002 | Blum et al. | 351/159 |
| 2004/0031903 A1 * | 2/2004 | Kiyoshi et al. | 250/201.1 |

FOREIGN PATENT DOCUMENTS

| | | |
|---|---|---|
| FR | 2 681 443 | 3/1993 |
| WO | WO 93/08774 | 5/1993 |
| WO | WO 97/48002 | 12/1997 |
| WO | WO 02/49554 A1 | 6/2002 |

* cited by examiner

LIGHT SENSOR ARRANGEMENT FOR AUTO-DARKENING LENSES AND METHOD

CROSS-REFERENCE TO RELATED APPLICATION

This application claims the benefit of U.S. Provisional Application Ser. No. 60/486,091, filed Jul. 10, 2003, the entire disclosures of which are incorporated by this reference.

TECHNICAL FIELD

The present invention relates generally, as indicated, to a light sensor arrangement for auto-darkening lenses and method, and, more particularly, to a light directing arrangement for directing light to light sensors of an auto-darkening lens.

BACKGROUND

In an exemplary auto-darkening lens, such as, for example, an auto-darkening lens used in a welding helmet, welding goggles, respirator systems, and in other systems in which it is desired automatically to control light transmission, a shutter is controlled to respective dark and/or bright or clear states (or modes) and possibly to intermediate states therebetween. The shutter may be, for example, a liquid crystal shutter or some other shutter that controls light transmission, for example, without affecting image characteristics of light transmitted through the shutter. Operating circuitry operates the shutter to assume the respective states, and a light sensor (sometimes referred below as "photosensor") senses light conditions and provides an input to the operating circuitry to operate the shutter in response to the sensed light conditions. The photosensor may be a photocell, a light sensitive diode, or some other device that senses light and provides an output representative of that light. The light may be in the visible, ultraviolet, infrared, or some other spectrum range or combination of ranges.

In an exemplary auto-darkening lens the sensor is placed at the front of a support structure or housing in which the shutter is mounted or the sensor may be in the support structure (e.g., housing), which is provided with an access opening to allow light to reach the sensor. The location at which the sensor is mounted on or in the support structure may be selected to allow the light sensor to receive incident light that is representative of light that impinges on the shutter. It is desirable that the intensity of the light incident on the sensor would be representative of the light incident on the shutter. However, as the sensor is on or in the support structure, it actually is spaced relatively far from the viewing window provided by the shutter; and, therefore, the accuracy of sensing light on the shutter is less than optimum. Also, during use of an auto-darkening lens it is possible that a sensor may become blocked from direct light, for example, as a wearer moves an arm or a tool between the sensor and a source of bright light, such as, for example, light that occurs in the course of a welding process. It also is possible that some other object, e.g., a pole or other obstruction, may be in or come into the light path between such a bright light source and the auto-darkening lens sensor. Such blocking of bright incident light from the sensor may occur even though such light still may be impinging on the viewing window of the shutter. Such blocking of the sensor may prevent the auto-darkening lens from reliably switching to the dark state or may allow the shutter to return to a clear state although bright light continues to be produced by the light source.

In the description herein reference will be made to a lens (also sometimes referred to as "welding lens," "welding filter," " "shutter," and the like, and to an automatically darkening lens (sometimes referred to as auto-darkening lens) that is able to operate automatically to control transmission of light. The lens may be a light shutter type of a device that is able to control light transmission without distorting, or at least with relatively minimal distortion, of the light and the image characteristics carried by the light or represented by the light. Therefore, when a person looks through the lens, the image seen would be substantially the same as the image seen without the lens, except that the intensity of the light transmitted through the lens may be altered depending on the operative state of the lens. The lens may be used in a welding helmet, and the lens may be used in other types of devices, such as goggles, spectacles, face masks, e.g., for industry (such as in an industrial plant or to protect outdoor or indoor electrical workers), for dentistry to protect the face of a dentist in the operative, respirator systems, nuclear flash eye protection devices, and other types of helmets, etc. Such devices usually are employed to protect the face or the eyes of a person, as is known, for example, in the field of welding and in other fields, too. Further, the lenses may be used in various other places to protect workers from bright light that could present a risk of injury.

For the purposes of providing eye protection, usually a welding lens provides light blocking characteristics in the visible, infrared and/or ultraviolet wavelength ranges. The actual ranges may be determined by the components of the lens, the arrangement of those components, and so forth. One example of such a welding lens is U.S. Pat. No. 5,519,522. The lens assembly disclosed in that patent includes several liquid crystal cell light shutters, several plane polarizers, and a reflector or band pass filter, which is able to reflect ultraviolet and infrared electromagnetic energy and possibly also some electromagnetic energy in the visible wavelength range. The several liquid crystal cells, for example, may be birefringent liquid crystal cells sometimes referred to as surface mode liquid crystal cells or pi-cells.

As will be described further below, the present invention may be used in a variable optical transmission controlling device. The device is described in detail with respect to use in a welding helmet. However, it will be appreciated that the device may be employed in other environments and in other devices and systems for controlling transmission of electromagnetic energy broadly, and, in particular, optical transmission. As used herein with respect to one example, optical transmission means transmission of light, i.e., electromagnetic energy that is in the visible spectrum and also may include ultraviolet and infrared ranges. The features, concepts, and principles of the invention also may be used in connection with electromagnetic energy in other spectral ranges.

Examples of liquid crystal cells and shutters (the terms liquid crystal cell and liquid crystal shutter may be used interchangeably and equivalently herein unless context indicates or implies otherwise), lenses using them and drive circuits are described in U.S. Pat. Nos. 5,208,688, 5,252,817, 5,248,880, 5,347,383, and 5,074,647. In U.S. Pat. No. 5,074,647, several different types of variable polarizer liquid crystal devices are disclosed. Twisted nematic liquid crystal cells used in an automatic shutter for welding helmets are disclosed in U.S. Pat. Nos. 4,039,254 and Re. 29,684. Exemplary birefringent liquid crystal cells useful as light shutters in the present invention are disclosed in U.S. Pat. Nos. 4,385,806, 4,436,376, 4,540,243, 4,582,396, and Re. 32,521 and exemplary twisted nematic liquid crystal cells and displays are disclosed in U.S. Pat. Nos. 3,731,986 and 3,881,809. Another type of liquid crystal light control device is known as a dyed liquid crystal cell. Such a dyed cell usually includes nematic liquid crystal material and a pleochroic dye that absorbs or transmits light according to orientation of the dye molecules. As the dye molecules tend to assume an alignment that is relative to the alignment of the liquid crystal structure or directors, a solution of liquid crystal material and dye placed between a pair of plates will absorb or transmit light depending on the alignment of the liquid crystal material. Thus, the absorptive characteristics of the liquid crystal device can be controlled as a function of applied electric field.

As is disclosed in several of the above patents, the respective shutters may have one or more operational characteristics (sometimes referred to as modes or states). One example of such an operational characteristic is the shade number; this is the darkness level or value of the shutter when it is in the light blocking mode (dark state). Another exemplary operational characteristic is the delay time during which the shutter remains in a dark state after a condition calling for the dark state, such as detection of the bright light occurring during welding, has ceased or detection thereof has terminated or been interrupted. Still another operational characteristic is sensitivity of the detection circuit and/or shutter to incident light, for example, to distinguish between ambient conditions and the bright light condition occurring during a welding operation, and sensitivity also may refer to shutter response time or to the time required for the circuitry associated with the lens to detect a sharp increase in incident light (e.g., due to striking of the welding arc, etc.) and to switch the lens from the clear state to the dark state. Even another characteristic, which may be considered an operational characteristic, is the condition of the battery or other power source for the shutter, such as the amount of power remaining, operational time remaining until the power source becomes ineffective, etc. In the past various of the operational characteristics of such shutters have been adjustable or fixed.

Dynamic operational range or dynamic optical range is the operational range of the lens between the dark state and the clear state, e.g., the difference between the shade numbers of the dark state and the clear state.

An example of a "welding lens with integrated display and method" is disclosed in U.S. Pat. No. 6,067,129. In the invention disclosed therein the current operational characteristics of the shutter can be displayed and can be selectively changed by operating one or more switches. The switches may be flexible membrane switches, microswitches, or another type of switch.

The present invention is useful for eye protection by an automatic darkening light shutter in a helmet or goggle assembly or in another device, if desired. The switching mechanism for powering the light shutter on and off and/or for selecting operational characteristics may be an integral part of the light shutter and/or frame assembly or other component or portion thereof.

The light shutter, photosensor arrangement and/or control of the present invention may be used in a variety of embodiments and applications. The shutter is adjustable to control light, i.e., to increase or to decrease the amount of the incident light that is transmitted through the shutter. When welding is not occurring, for example, the shutter in a welding helmet may be substantially optically clear or transmissive or at least minimizes its attenuation of light. When welding is occurring, the shutter may be dark or closed to reduce the amount of light transmitted therethrough in order to protect the eyes of the person performing the welding and to maximize his or her viewing comfort. In both cases, though, the image characteristics of the light preferably remain intact. A photosensitive device may be used to sense the intensity of light impinging in the area of the shutter so as to provide an input to a drive circuit for the shutter in order to control opening and closing thereof.

The disclosures of the patents identified herein are incorporated in their entirety by reference.

SUMMARY

An aspect of the invention is to reduce the distance between the light sensors and the viewing window area of a controllable shutter for an auto-darkening lens.

Another aspect is to improve the accuracy of light sensing for an auto-darkening lens.

Another aspect is to reduce the amount of wiring and/or other parts of an auto-darkening lens system by using a light director to direct light from one or more locations in proximity to a controllable light shutter to a sensor to which operating circuitry for the shutter is responsive.

According to an aspect the invention relates to an auto-darkening lens including a controllable shutter having at least a relatively dark state and a relatively clear state, operating circuitry to operate the controllable shutter to such states, a sensor to sense incident electromagnetic energy, and a light guide to receive incident electromagnetic energy in proximity to the controllable shutter to guide such electromagnetic energy to the sensor.

Another aspect relates to a control for an auto-darkening lens that has a controllable shutter providing a viewing window, including a light responsive control to control a controllable shutter, and a light director having a light inlet positionable in a viewing window area of a controllable shutter for directing light to the light responsive control.

Another aspect relates to a control for an auto-darkening lens that has a controllable shutter providing a viewing window, including a light responsive control to control a controllable shutter, and a light director having a light inlet positionable laterally adjacent a viewing window area of a controllable shutter for directing light to the light responsive control.

Another aspect relates to an auto-darkening lens including a housing, a photosensor, a controllable shutter controllable in response to light sensed by the photosensor, and a light director for directing light from an area at least one of in a viewing window of the controllable shutter and laterally adjacent the viewing window.

Another aspect relates to a method of controlling an auto-darkening light shutter, which provides a viewing window, including detecting light incident on the viewing window in the area of the viewing window.

Another aspect relates to a method of controlling an auto-darkening shutter that provides a viewing window, including directing light from both lateral sides of the viewing window to a photosensitive control as a representation of light incident on the viewing window thereby to control operation of the auto-darkening shutter.

Another aspect relates to a control for an optical device that has a controllable shutter providing a viewing window, including a light responsive control to control a controllable shutter, and a light director having a light inlet within a viewing window area of such a controllable shutter for directing light to the light responsive control.

Another aspect relates to a method of controlling a light shutter that provides a viewing window, including directing light from at least partly within the viewing window to a photosensitive control as a representation of light incident on the viewing window thereby to control operation of the shutter.

These and other objects, features, advantages and functions of the invention will become more apparent as the following description proceeds.

It will be appreciated that although the invention is described with respect to one or more embodiments, the scope of the invention is limited only by the claims and equivalents thereof. It also will be appreciated that if the invention is described with respect to several embodiments, features of a given embodiment also may be used with one or more other embodiments.

Also, although the invention is described with respect to a welding shutter (also known as a light shutter) used in a welding helmet for eye protection therein, it will be appreciated that the various features of the invention may be used in conjunction with other devices and functions.

To the accomplishment of the foregoing and related ends, the invention, then, comprises the features hereinafter described in the specification and particularly pointed out in the claims, the following description and the annexed drawings setting forth in detail certain illustrative embodiments of the invention, these being indicative, however, of but several of the various ways in which the principles of the invention may be suitably employed.

DESCRIPTION

Figure 1:
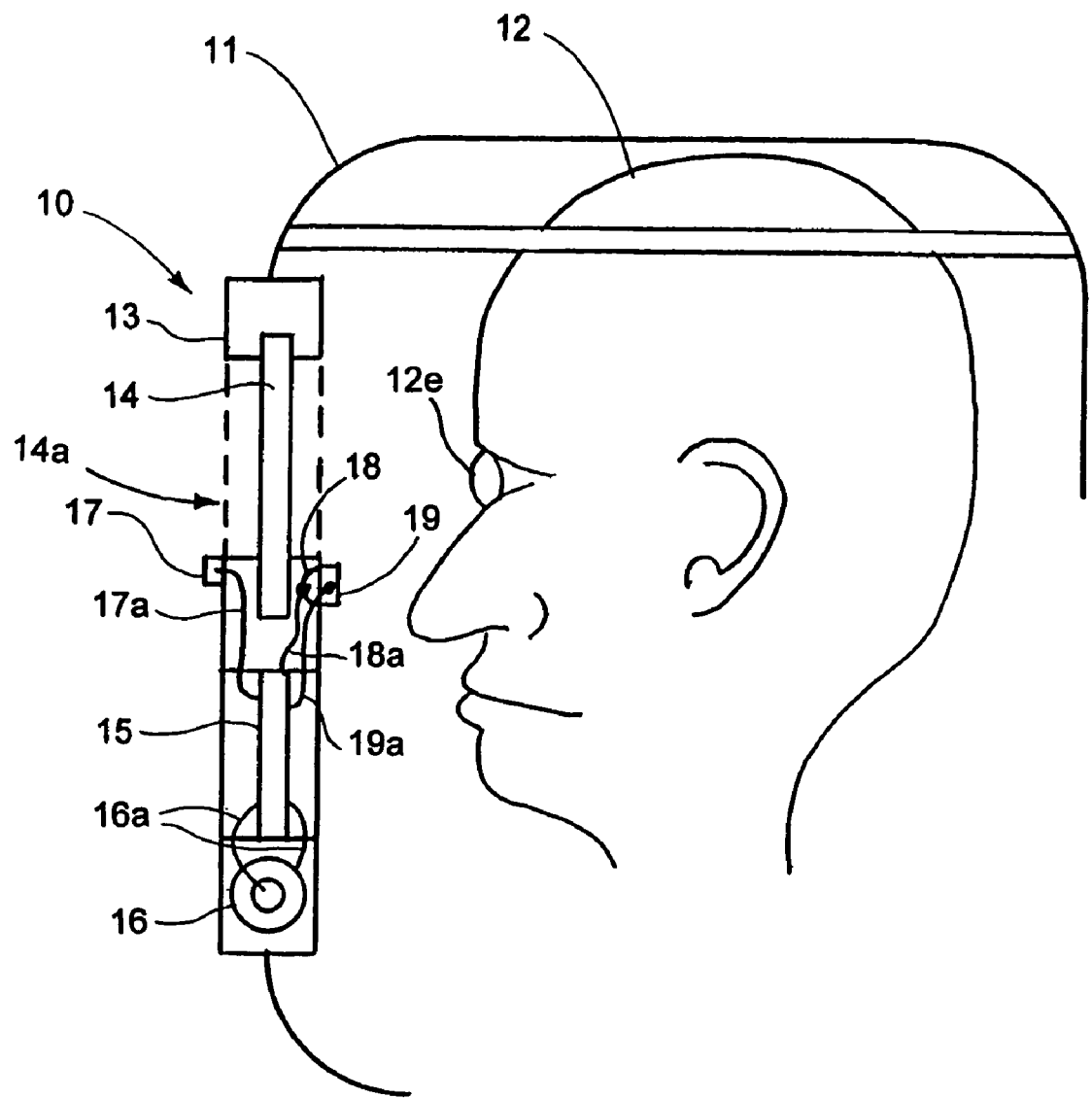
FIG. 1 is a schematic side elevation view, broken away, of an auto-darkening lens in a welding helmet in place on the head of a wearer.

Referring, now, to the drawings, wherein like reference numerals designate like parts in the several figures and primed reference numerals designate parts that are similar to parts designated by the same unprimed reference numeral, and initially to FIG. 1, an auto-darkening lens 10 is illustrated in a welding helmet 11 in position on the head of a wearer 12 (sometimes referred to as a user). In the description below primed reference numerals are used to represent parts that are similar to parts that are designated by the same unprimed reference numeral. In the description below reference to directions, such as horizontal, vertical, left, right, up, down, is for relative reference only and is not intended to be limiting.

The auto-darkening lens 10 includes, for example, a support structure or housing 13, a variable light transmission shutter 14 mounted with respect to the support structure, operating circuitry 15 and power supply 16. Connections 16a couple the power supply 16 to provide power to the operating circuitry 15. Associated with the operating circuitry 15 is a photosensor 17, which is coupled to the operating circuitry by connections 17a, to sense occurrence of a need for or a condition requiring the auto-darkening lens 10 to darken or to lighten, e.g., to decrease light transmission during welding or to increase light transmission in the absence of welding. The operating circuitry 15 operates the auto-darkening lens to various conditions of light transmission. Several control buttons and switches schematically shown at 18 in FIG. 1 are coupled by connections 18a to the operating circuitry 15 and may be operated by the wearer 12 to turn on the operating circuitry 15 to operate the shutter 14, e.g., to adjust desired shade, to set delay time, to set sensitivity, etc. As an example, the switches 18 may be membrane switches. The operating circuitry 15, power supply 16, photosensor 17, and buttons and switches 18 may be mounted on, in or part on and part in the support structure 13 or may be otherwise located, as may be desired. In using the auto-darkening lens 10 in the welding helmet 11, a wearer 12 may turn on the power and set the desired dark shade of the shutter 14 by using the buttons and switches 18; and the wearer then puts the welding helmet 11 on the head with the shutter in front of the eyes for viewing work. The shutter 14 may be in its relatively clear or high light transmission condition (or state) to allow the wearer to view the work; and upon sensing occurrence of welding, the photosensor 17 indicates the same to the operating circuitry to cause the shutter to assume a dark or relatively reduced light transmission condition (or state). When welding ceases, the operating circuitry allows the shutter to return to the relatively clear condition.

Indicators 19 indicate operating conditions of the auto-darkening lens 10. The indicators 19 may be coupled, as at 19a, to the operating circuitry or to some other device that operates the indicators. Examples of operating conditions may include, without limitation, the current shade or light transmitting condition of the shutter 14, e.g., is it clear or dark; reserve power supply power level, e.g, how much charge remains in the power supply (such as a battery) before becoming unable to supply adequate power to the operating circuitry 15 to operate the shutter 14; whether power from an external source is connected for operating the auto-darkening lens; whether the auto-darkening lens 10 is on, e.g., is receiving power to the operating circuitry 15; what shade level has been set, e.g., by the buttons and switches 18; what delay time and/or sensitivity has been set, e.g., by the buttons and switches 18; etc.

The indicators 19 may be of the type that provide a light output. For example, each indicator may be a light emitting diode, an organic light emitting diode, an incandescent bulb, a combination of a light source and a light modulating device, such as a liquid crystal light modulator, or other type of device that provides a light output or indication based on light in response to an appropriate energization. The light output may be the generating or emitting of light by a given light source or it may be modulation of the light from a light source. The light output may be white, may be of a given color, or may be of different respective colors. Operation of the indicators 20 may be provided by the operating circuitry 15. For example, the operating circuitry may provide respective signals and, if needed, power to cause respective indicators to provide a light output, to modulate light from a light source, to provide respective colors of light, etc. Such respective signals from the operating circuitry 15 may indicate the above-mentioned operating conditions of the auto-darkening lens 10 and/or other information that may be of interest, useful and/or needed by the wearer 12.

Figure 2:
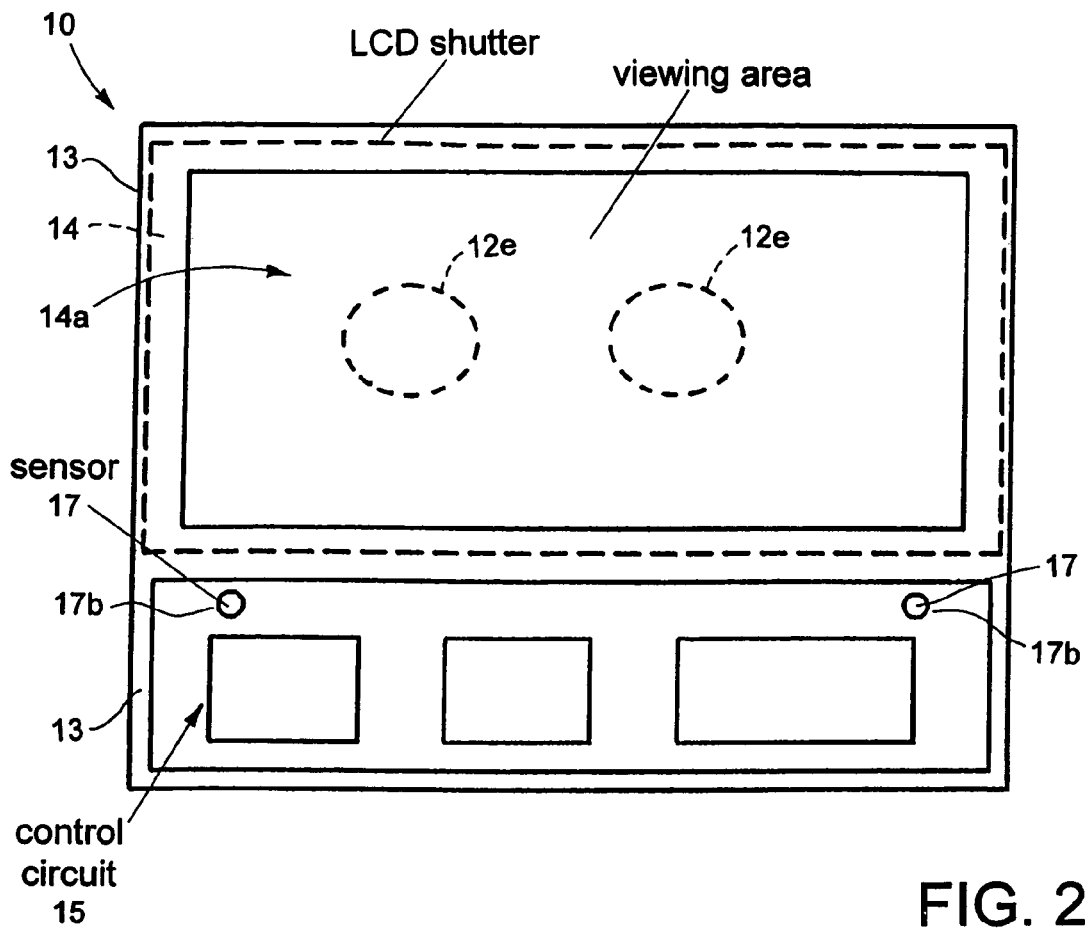
FIG. 2 is a front view of a conventional auto-darkening lens.
Figure 3:
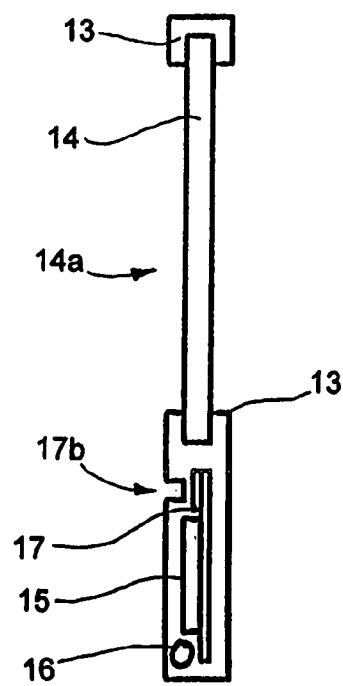
FIG. 3 is a side elevation view, partly broken away, of the auto-darkening lens of FIG. 2.

Turning to FIGS. 2 and 3, a conventional auto-darkening lens 10 is illustrated. The auto-darkening lens 10 includes a support structure or housing 13, controllable light shutter 14 that provides a viewing window 14a, operating circuitry 15 and power supply 16, and in this case, two photosensors 17 (sometimes referred to herein as sensors). The photosensors 17 are mounted on a common circuit board 15a supporting the operating circuitry 15. Windows or openings 17b in the support structure 13, for example, in the front face thereof, provide a path for light to reach the two photosensors 17, respectively. The openings 17b and photosensors 17 are located laterally spaced apart at the sides of the front face of the auto-darkening lens 10 support structure 13 beneath the liquid crystal shutter and, thus, beneath the viewing window 14a, as is seen in FIGS. 2 and 3, for example.

Figure 4:
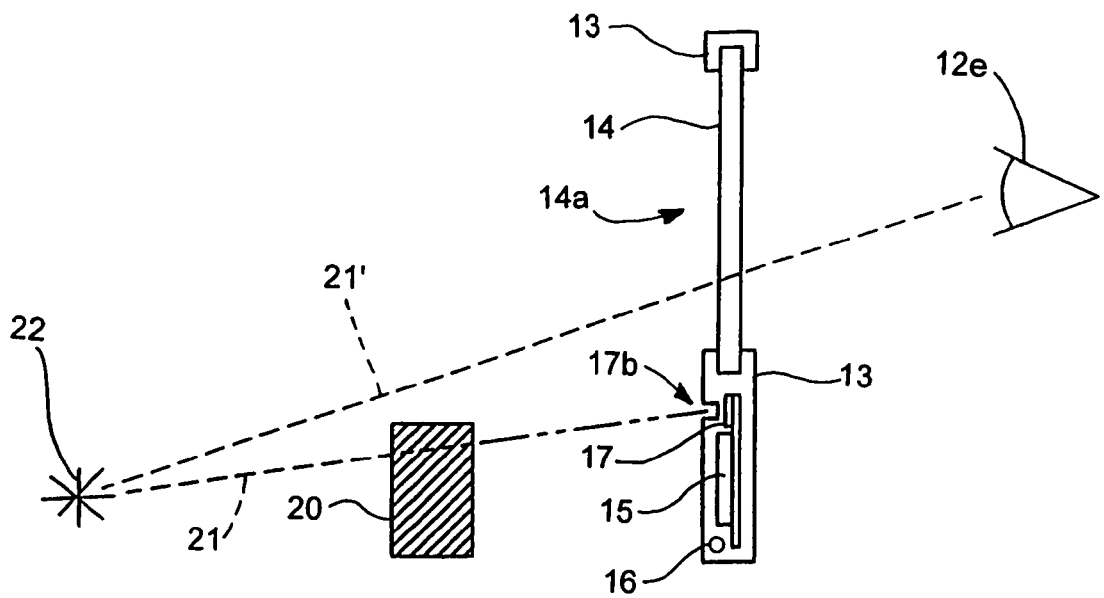
FIG. 4 is a side elevation view of the auto-darkening lens of FIGS. 2 and 3 illustrating a blockage in the light path to the photosensor of the auto-darkening lens.

In FIG. 4 is illustrated a possible problem encountered using the auto-darkening lens 10 wherein an object 20 is in the light path 21 between a point source of light 22, such as occurs in the course of the welding process, and the photosensor(s) 17 of the auto-darkening lens 10. Such path 21 is blocked by the object 20. However, light path 21' from the point source 22 to the viewing window 14a through the shutter 14 shows light from the point source reaching the eye 12e of a wearer or user 12 of the auto-darkening lens 10. Since the object 20 is blocking the light path to the sensor(s) 17, the sensor(s) would not receive the high intensity or bright light from the point source 22 and may either not cause darkening of the shutter 14 or may allow the shutter to release or to assume a clear state from the prior existing dark state, thus leaving the eye(s) 12e of the wearer 12 relatively unprotected by the shutter 14. The object 20 may be a pole, wall, tool, arm of a wearer, etc.

Figure 5:
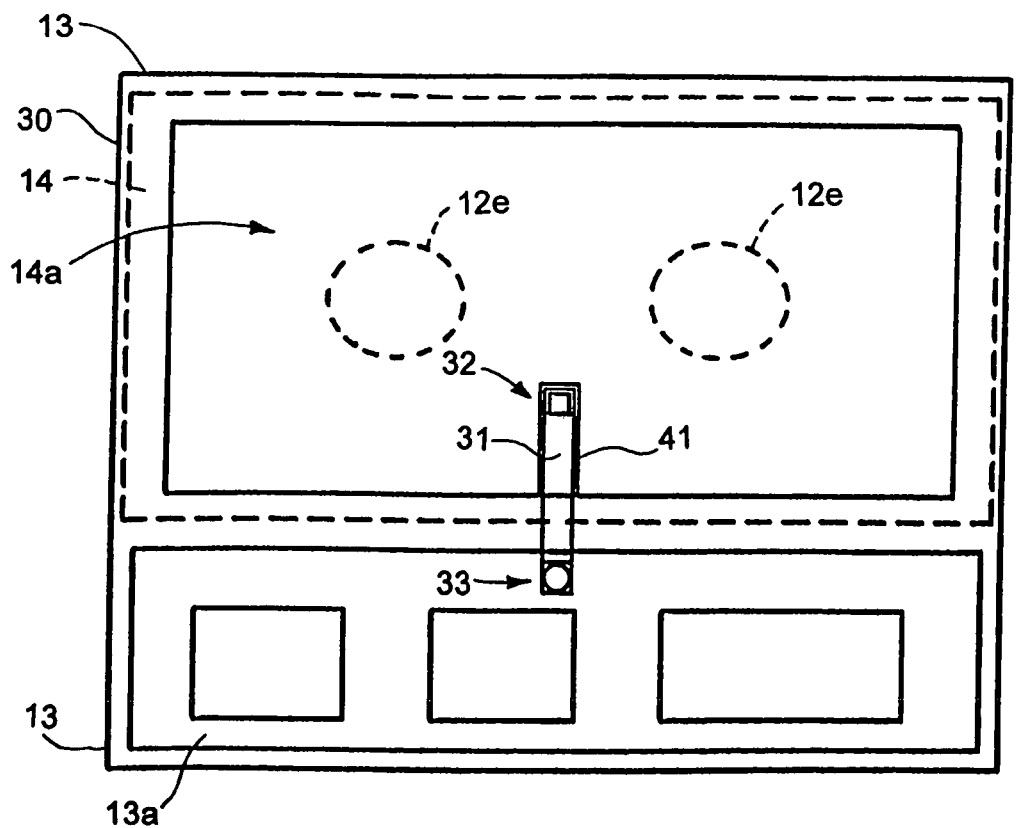
FIG. 5 is a front view of an auto-darkening lens having a light directing arrangement of the invention.
Figure 6:
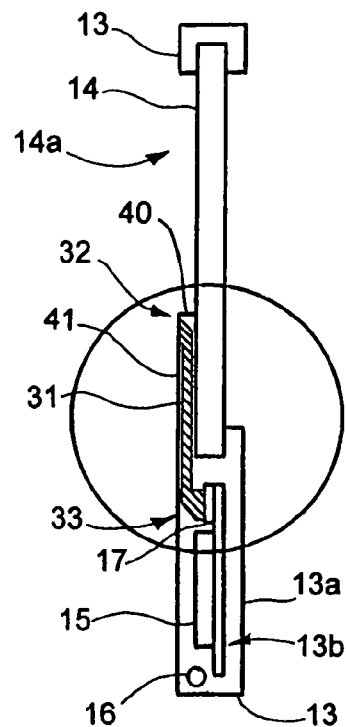
FIG. 6 is a side elevation view, partly broken away, of the auto-darkening lens of FIG. 5.
Figure 7:
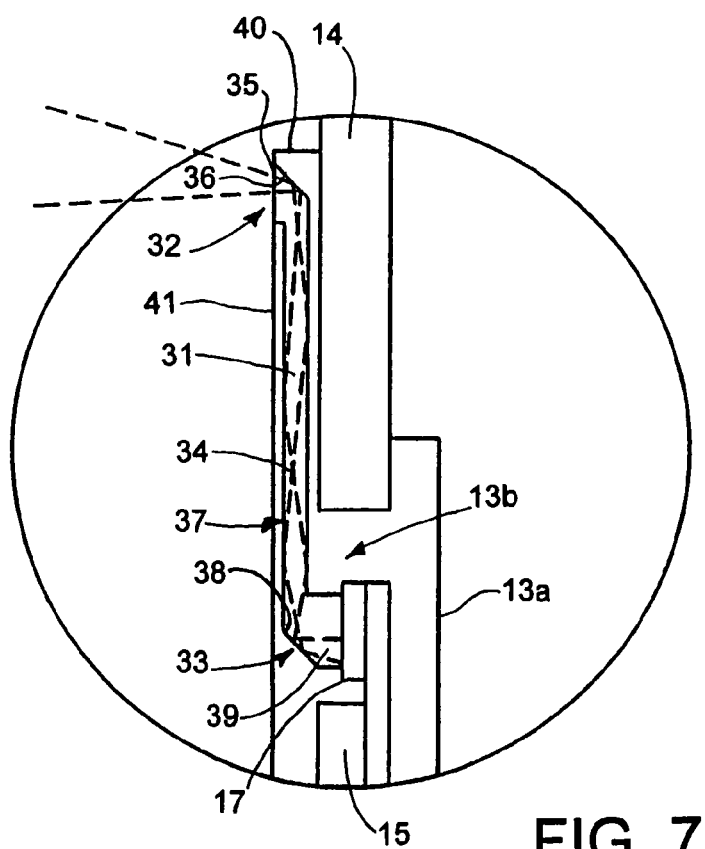
FIG. 7 is an enlarged fragmentary view in side elevation showing the light path to a sensor of the auto-darkening lens of FIGS. 5 and 6.

Referring to FIGS. 5-7 an auto-darkening lens (sometimes abbreviated below as "ADL") 30 is illustrated. The ADL 30 includes a support structure or housing 13 and controllable shutter 14 that provides a viewing window 14a through which a user may look when the ADL is in use in a helmet 11 or in goggles or in some other device. The ADL 30 also includes operating circuitry 15, power supply 16, a photosensor 17, and a light director 31.

The light director 31 is so oriented and positioned relative to the viewing window 14a of the controllable light shutter 14 of the ADL 30 as to pick up or to receive incident light that is the same or substantially the same as the light that impinges on the controllable light shutter. The light director 31 has a light inlet 32, which receives incident light, and a light outlet 33, which directs light to the photosensor 17. The light inlet 32 and light outlet 33 are in optical relation so that the inlet 32 directs light to the outlet 33 to be directed to the photosensor 17. In an embodiment it may be desirable to locate the light director 31 light inlet 32 as close as is reasonably possible to the area of the shutter 14 where a wearer 12 ordinarily would view through the shutter.

Thus, it will be appreciated that the light director 31 redirects light from near the visual path along which a wearer would look through the viewing window 14a of the controllable shutter 14 to the light sensor. The use of a light director 31 allows placement of the sensor input, e.g., the light inlet 32 of the light director, closer to the wearer's visual path than previously was possible with sensors located, for example, in the manner illustrated in FIG. 2. Also, using a prism or other light director 31 effectively to move the light inlet of the sensor 17 allows the use of a single more reliable and more expensive sensor without increasing the cost over that of two sensors, e.g., as are shown in the auto-darkening lens 10 of FIG. 2, while still reducing the likelihood that the sensor would be blocked from the incident light that is intended to be detected.

In the illustrated ADL 30 the light director 31 is a light pipe type device. An example of a light pipe device is a plastic, polymer, or other material that conducts light through it along a given path. Such a light pipe may retain light therein using principles of total internal reflection or some other principle to direct light therealong from the inlet to the outlet. The light pipe may be a space between the inlet and outlet; and in such case the inlet and outlet may have respective reflectors or the like to receive and to direct light from the inlet to the outlet. Thus, the light pipe may be a solid material, a liquid material in an appropriate container, and/or an air space through which light is conducted between the inlet 32 and the outlet 33. The mentioned reflectors associated with the light pipe may be prisms or other light reflecting device.

In the illustrated example of ADL 30, the light director 31 includes a solid light conducting rod 34 that has a light inlet face 35 at the inlet 32 in which light may enter the light conducting rod and a reflecting surface 36 for reflecting received light from the face 35 along the elongate light pipe extent 37 to a further reflecting surface 38 and from there to the light outlet face 39. The angle of view or aperture of the inlet face 35 may be designed to obtain a desired field of view and/or angle of view for the light pipe. The size, shape and orientation of the outlet face 39 may be related to the light input acceptance characteristics of the photosensor 17, for example, to optimize light transfer from the light pipe to the photosensor with appropriate efficiency, e.g., minimal light loss.

The light inlet face 35 of the light director or light pipe 31 is located in the area of and in the path of light to the controllable shutter 14. In the illustrated example of FIGS. 5-7 the light inlet face is approximately at the lateral center of the viewing window 14a and vertically is approximately at about the same height or vertical location of the wearer's 12 eyes 12e, which are shown in dotted outline in FIG. 5, for example. As illustrated, the light inlet face 35 is approximately between the eyes of the wearer and at approximately the same vertical height as the wearer's eyes or in any even not too far from that vertical height; it is difficult to block that light inlet face from the standpoint of where the wearer's hands would be during welding or where some other work for which the ADL is being used. The precise location of the light inlet face 35 may be changed as may be desired; however, it will be appreciated that the light inlet face 35 is in closer relation to the wearer's eyes 12e than would be the photosensors 17 in the auto-darkening lens 10 of FIGS. 2-4. Since the light inlet face 35 is relatively closer to the location of the eyes 12e, if the eyes receive bright light from the point source 22, for example, then it is likely that the light inlet face 35 also will receive such bright light. Furthermore, although it is possible that an arm or other obstruction may block the photosensors 17 of the auto-darkening lens 10 that are relatively remotely located from the viewing window 14a, it is unlikely that welding would be carried out by the wearer 12 with the eyes 12e blocked; therefore, it would be likely that the light director 31 would be receiving and directing to the photosensor 17 welding light or other bright light from which the wearer would want to be protected.

As is seen in FIGS. 5-7, the support housing 13 retains the controllable shutter 14, for example in a groove or slot 40 (FIG. 7). An extension 41 of the support housing 13 extends vertically from the major extent of the support housing, e.g., that portion shown in FIG. 7 at 13a. Such extension 41 provides support and protection for the light director 31, for example. If the light director were self-supporting it may be possible to eliminate the extension 41. Also, if desired other structure may be used to support and protect, if needed, the light director 31. The described arrangement of extension 41, support housing 13, and light inlet face 35 of the light director 31 allows the light inlet face to be placed rather proximate the area in the viewing window 14a where the eyes of a viewer would be looking through the viewing window without having to make any complex cutouts or other design features in the controllable shutter 14.

The mentioned major extent 13a of the support housing includes a hollow space 13b within which the operating circuitry 15 and power supply 16, e.g., a battery, are located. As is illustrated in FIG. 7, the photosensor 17 is mounted on or with respect to a circuit board 15a of the operating circuitry 15 and the outlet face 39 of the light director 31 is oriented to direct light to the photosensor 17. Thus, the photosensor 17 is located in a relatively protected place in the space 13b, on the one hand, and receives light that is incident on the controllable shutter and light inlet face 35, on the other hand. Being able to detect light from the area that is encompassed by the controllable shutter or at least from a part of such area, helps to assure that the photosensor will provide inputs to the operating circuitry accurately representing the character of the light that is incident on the controllable shutter 14, for example, in the area of the wearer's eyes 12e; and the operating circuitry 15 will operate the controllable shutter to respective clear and dark states (or possibly intermediate states) as necessary depending on light impinging on the controllable shutter.

It will be appreciated that although a single light director 31 is illustrated in FIGS. 5-7, a number of similar light directors may be used. For example, such light directors may be located at spaced apart lateral locations along the width of the viewing window 14a.

Figure 8:
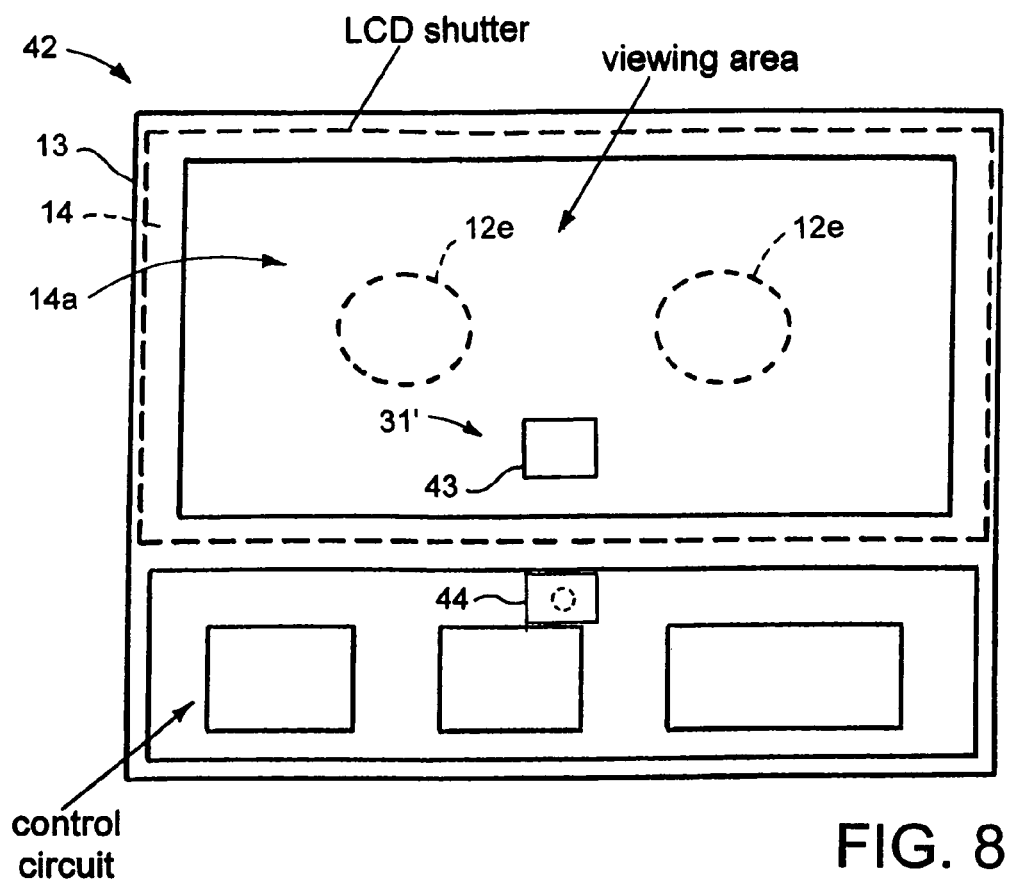
FIG. 8 is a front view of an auto-darkening lens with a reflector or prism type light director.
Figures 9A, 9B:
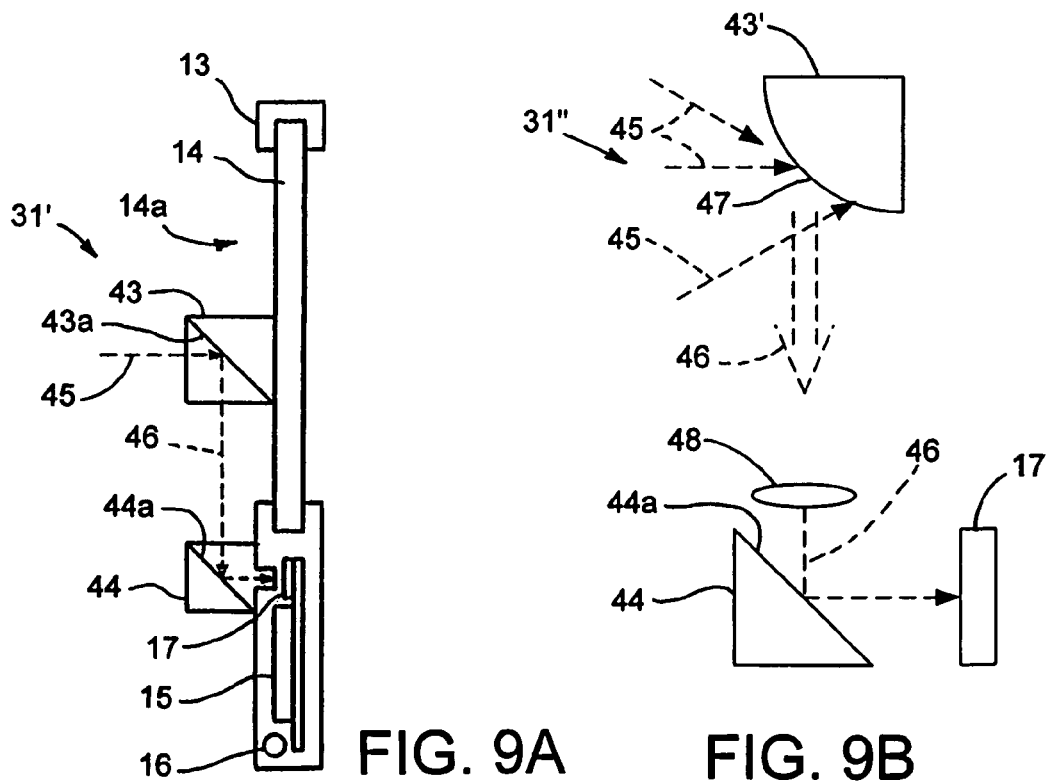
FIG. 9A is a side elevation view of the auto-darkening lens of FIG. 8.
FIG. 9B is a schematic side elevation view of a light director arrangement including a reflector with a convex curved reflective surface and a collection lens in the directed light path.

In FIGS. 8 and 9A is illustrated an example of another auto-darkening lens (ADL) 42 with a light director 31'. The ADL 42 is similar to the ADL 30 except the light director 31' includes a pair of reflectors 43, 44 instead of a light pipe. In the illustration of FIGS. 8 and 9A and 9B, the reflectors 43, 44 are illustrated as prisms that have a reflective surface 43a, 44a; however it will be appreciated that various types of reflectors may be used to reflect light received along light path 45 to light path 46 for sensing by the photosensor 17. Therefore, reference to reflectors or to prisms functionally for reflecting light are considered equivalent.

The prism 43 is located in the area of the viewing window 14a in the visual path of a viewer or wearer of the ADL 42, e.g., wearing a welding helmet, goggles, eyeglasses, safety glasses, etc., in which the ADL 42 is mounted or positioned. As is seen in FIGS. 8 and 9A the prism 43 is approximately at the height of or somewhat below the viewing area of the wearer's eyes 12e and is approximately at a location between the wearer's eyes. Incident light 45, e.g., from a welding process, is reflected by the prism 43 as light (or light path) 46 to the prism 44, which in turn reflects the light 46 to the sensor 17 to operate the operating circuitry 15 to cause the controllable shutter to assume a dark state.

FIG. 9B shows a prism 43' that may be used in the ADL 42 (FIGS. 8 and 9A) in place of the prism 43. The prism 43' has a convex curved reflective surface 47 to receive incident light 45 over a relatively wide acceptance angle and to reflect the incident light along light path 46 to the prism 44 and from there to the photosensor 17 (FIGS. 8 and 9A). The prism 43' would have a wider acceptance angle for incident light 45 than ordinarily would be the acceptance angle for a planar reflective surface. The convex curved reflecting surface 47 tends to collect light or to receive light over a relatively wide acceptance angle for reflection by the reflector or prism 43 (or reflector) to the reflector 44 and from there to the photosensor 17.

As is shown in FIG. 9B, a lens 48, such as a plano-convex lens, may be in the light path 46 to the reflective surface 44a of reflector or prism 44. The lens 48 tends to limit the acceptance angle of light directed to the reflective surface 44a for directing light to the photosensor 17. Such a lens 48 may tend to increase the gain of the light director 31" by tending to limit the light that is directed to the photosensor 17 to light in the light path 46 from the reflector 43 (FIGS. 8 and 9A) or 43 (FIG. 9B). In a sense the lens 48 tends to reduce from reflection by the reflector 44 to the photosensor 17 the amount of ambient light that is not directed to the viewing window 14a (and reflected by the reflector 43 toward the reflector 44) of the auto-darkening lens.

Figure 10:
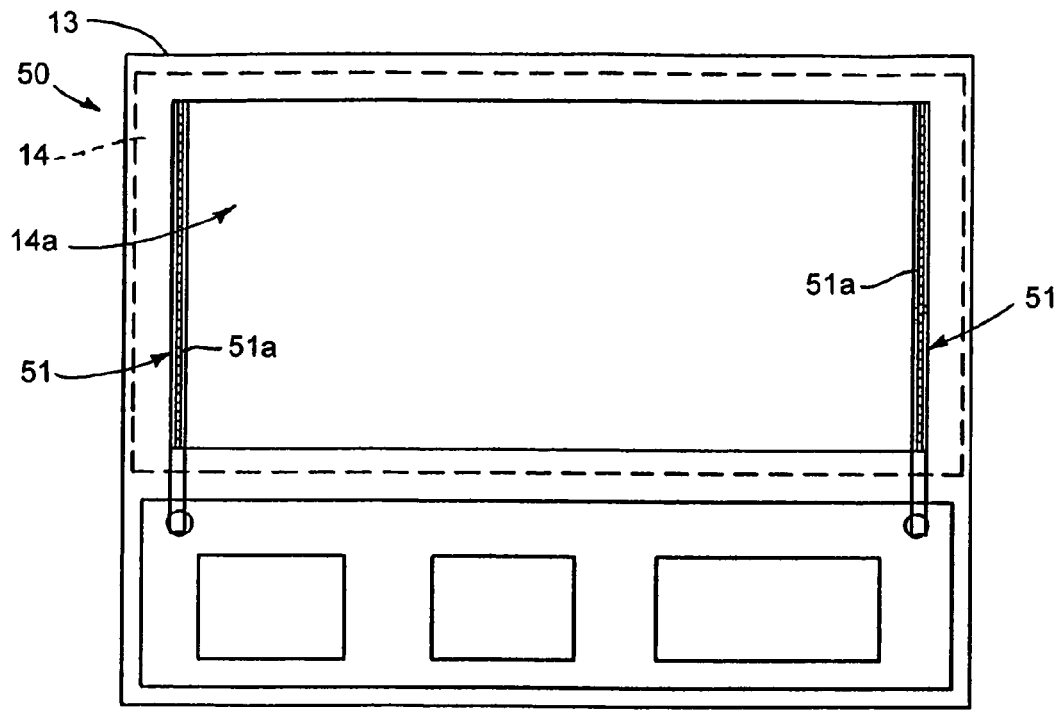
FIG. 10 is a front view of an auto-darkening lens with a multi-facet prism sensor arrangement light director of the invention.
Figure 11:
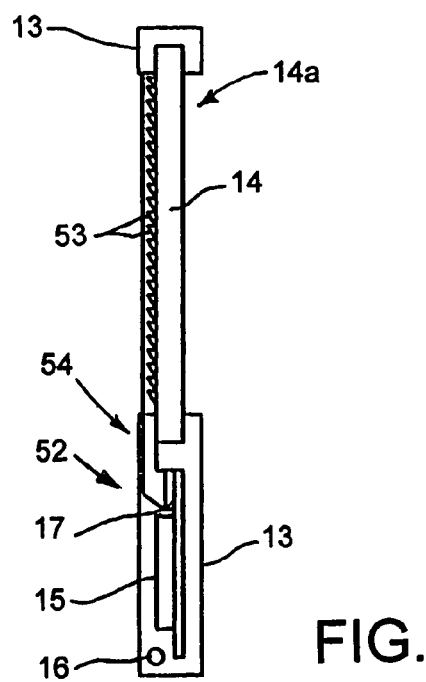
FIG. 11 is a side elevation view of the auto-darkening lens of FIG. 10.
Figure 12:
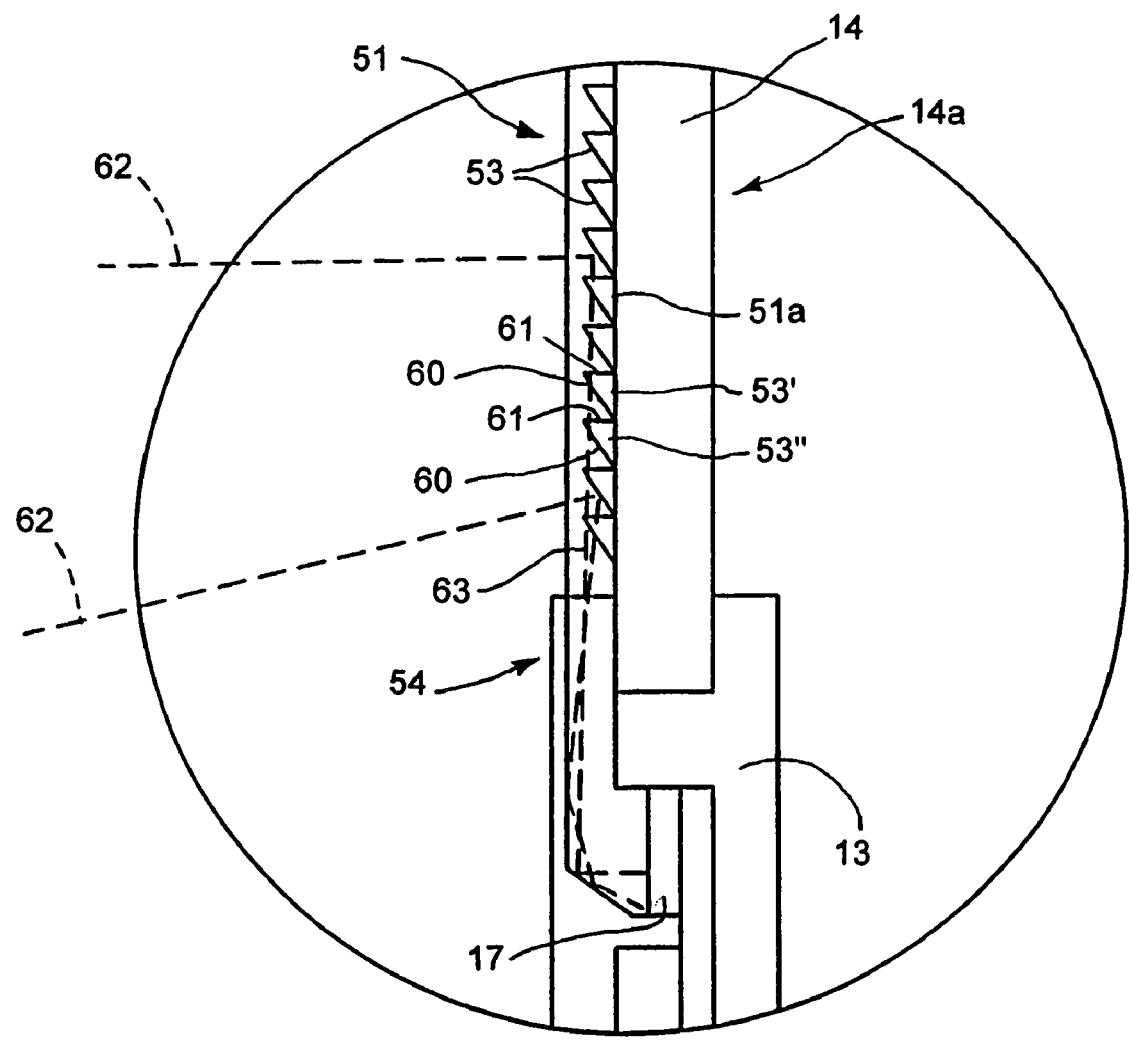
FIG. 12 is an enlarged fragmentary view showing the light path for part of the auto-darkening lens of FIGS. 10 and 11.

Turning to FIGS. 10-12, an auto-darkening lens (ADL) 50 with a pair of light directors 51 is illustrated. The light directors 51 are positioned and oriented adjacent the lateral sides of the viewing window 14a of the controllable shutter 14 to receive light and to direct the light to a photosensitive controller 52, that includes respective photosensors 17 and operating circuitry 15. The light directors 51 each includes one or more prisms 53. The light directors 51 also include a light conducting or directing portion 54 that directs light from the prism(s) to a respective photosensor 17. The light directing portion may be, for example, a light conducting rod or the like, one or more reflectors and an air gap, a hollow tubular light conductor, or some other device that directs light from a light director 51 to a photosensor 17.

In the illustration of FIGS. 10-12 the light directors are respective prism strips 51a, each having a number of prisms 53. The prism strips may be attached to the support housing 13 laterally adjacent the viewing window 14a of the controllable shutter 14. Adhesive material may be used to attach the prism strips 51a to the housing, although, if desired, other means may be used to effect the attachment. If desired, the prism strips may be positioned adjacent the top and/or bottom of the viewing window 14a in addition to or in place of the laterally adjacent prism strips.

The prism strips 51a receive light from a number of viewing angles, directions and locations relative to the viewing window 14a of the controllable shutter and direct light to the photosensors 17, which in turn provide input to the operating circuitry 15 to operate the controllable shutter to respective dark and clear states depending on light intensity, for example. Such arrangement of prism strips or of multiple prisms may in a sense provide the effect of having multiple sensors; yet, using the prism strips multiple sensors are unnecessary although the effect of multiple sensors detecting incident light from several locations in proximity to the controllable shutter 14 may be obtained.

As an example of respective prisms 53, consider prisms 53' and 53", each of which has a primary light reflecting surface 60 and a primary light transmitting surface 61. The light reflecting surface 60 acts as a light inlet to the prism strip 51a forming the light director 51. The angular orientation of the light reflecting surface 60 determines the angle of view or aperture over which incident light 62 that is impinging on the controllable shutter 14 and also on the light director 51 is directed to the photosensor 17. If desired, the angular orientation of light reflecting surface 60 for each prism may be the same relative to the major generally planar extent of the support housing 13 at the area of the support housing where the prism strip 51 is attached to the support housing. Alternatively, the angular orientation of the respective light reflecting surfaces 60 may be different, as may be desired. The material of which the prisms 53 are made, e.g., relative to air or other environment in which the prism strips 51 are used, may be such as to cause reflection of light incident on the light reflecting surface from a given angle or range of angles. However, if desired, a reflective coating may be applied to the light reflecting surface 61 to enable or to enhance light reflection for light of a given wavelength or range of wavelengths.

The light transmitting surface 61 tends to transmit light incident thereon as reflected thereto by a light reflecting surface 60. Such light transmission (e.g., light 63 shown in FIG. 12) may be adequate based on the optical characteristics of the material from which the prism strip 51 or respective prism 53', 53", for example, are made. However, if desired a coating may be applied to the light transmitting surface to enhance light transmitting characteristics through the interface thereof with the ambient environment, e.g., air. Furthermore, if desired, the angular relation of the respective light reflecting surface 60 of a given prism 53 relative to the direction of much of the light incident thereon via the light transmitting surface 61 of the same prism may be such as to tend to allow a satisfactory amount of such light to transmit through the material of which the prism is made and the associated light reflecting surface as to transmit to the light transmitting surface of the next subsequent prism, and so forth. Therefore, the light 62 incident on a number of prisms 53 of a light director 51 will be directed to the photosensor 17 as a representation of the intensity of the light incident on the controllable shutter 14. The angles, materials, etc. associated with the respective prism strips may be established according to the desired amount or percentage of the incident light on the prism strips that will reach the photosensor(s) 17. The operating circuitry sensitivity and the sensitivity of the photosensor(s) may be selected and/or adjusted to accommodate such percentage so that in response to the occurrence of a bright light caused, for example, by a welding process, the controllable shutter will be operated to the dark state; and if inadequate intensity light is detected, the controllable shutter would assume the clear or bright state.

Although the light directors 51 are shown directing light to respective photosensors 17, it will be appreciated that the light directors also may include an optical joining device, e.g., a light pipe or other device, that receives light from the respective light directors and combines that light for impingement on a common photosensor.

Figure 13:
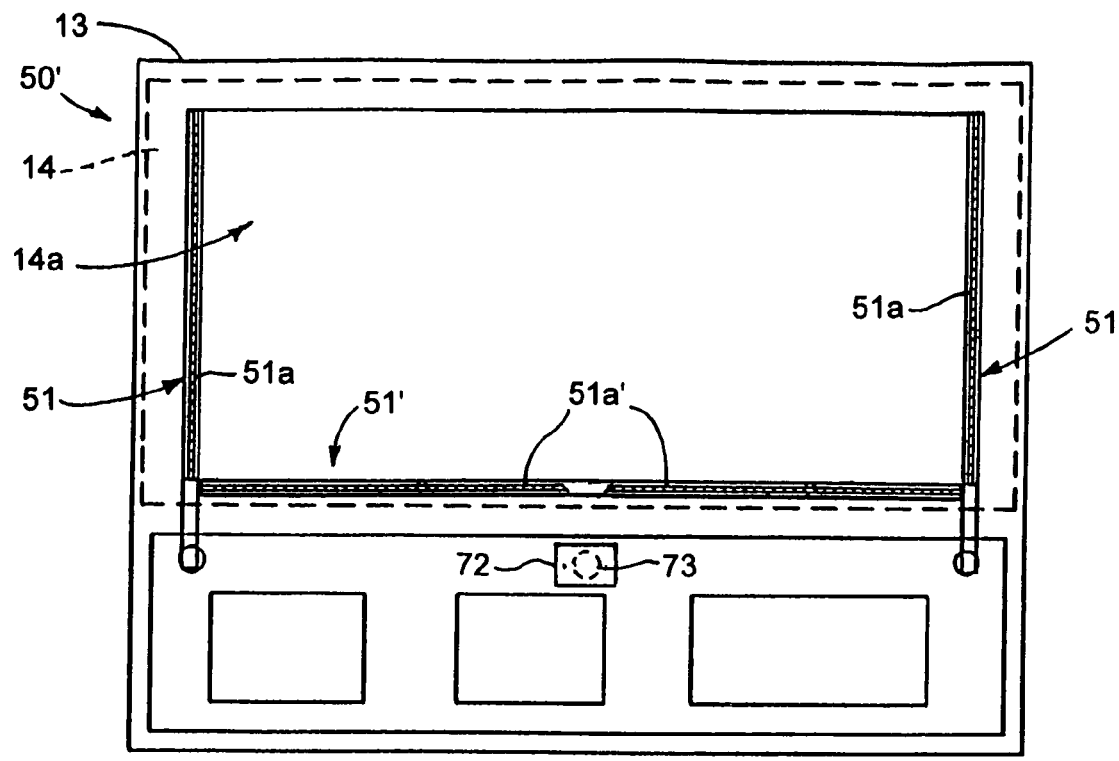
FIGS. 13 and 14 are a front view and an enlarged fragmentary view of an auto-darkening lens with a multi-facet prism sensor arrangement light director at the bottom area and, with respect to FIG. 13 also at the sides.
Figure 14:
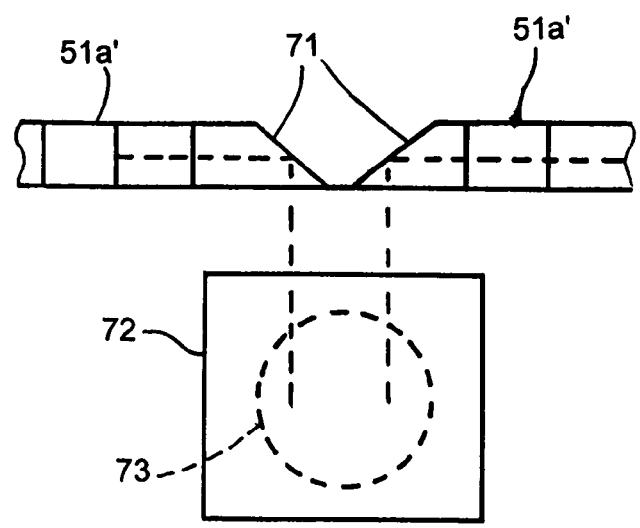

Turning to FIGS. 13 and 14, another ADL 50' is illustrated. The ADL 50' is similar to the ADL 50 shown in FIGS. 11 and 12. In the ADL 50' in addition to or in place of the light directors 51' in the form of prism strips 51a'; these may be similar to the light directors 51 and prism strips 51. The prism strips 51a' are at the bottom of the viewable area or window area of the light shutter 14 through which a user 12 would view welding, ambient conditions, or something else. Similarly, the prism strips 51a' could be at the top or elsewhere on the shutter 14 or its housing 13. The prism strips 51a' receive incident light and direct that light toward a center reflector 71, and the center reflector directs light to the photosensor 17, e.g., via another reflector 72 and an opening or aperture 73 in the housing 13. The reflectors 71, 72 and the opening/aperture 73 may be similar to and function in a manner similar to the reflectors and opening/aperture described above, e.g., reflectors 43, 44 and the opening leading from the reflector 44 to the photosensor 17 (see FIGS. 8, 9A and 9B). In FIG. 14 is illustrated an enlargement of the center reflector 71 and the reflector 72 for the ADL 50'. The center reflector 71 may be a molded or otherwise formed portion of each of the respective prism strips 51a', for example, as is illustrated. The center reflector 71 may be a separate reflector that is positioned to receive light from a respective prism strip 51a', if desired.

In use of the light director 51' arrangement, light is received by the respective prism strips 51a' and is reflected by respective reflective surfaces of the prism strips along the length of the prism strip toward the center reflector. At the center reflector 71 the light is reflected toward the reflector 72 and from there through the opening/aperture to the photosensor 17. Operation may be otherwise as was described above with respect to the illustrations of FIGS. 10 and 11. If prism strips 51a and 51a' are used with the same or with respective photosensors 17, the operating circuitry of the ADL 50' may take include logic, measuring circuitry, etc. to account for the light incident on the respective light directors 51, 51' to cause the light shutter to operate to provide dark or clear states (or possibly intermediate states).

INDUSTRIAL APPLICATION

It will be appreciated that the light directors and the control may be used with auto-darkening lenses of various types, such as, for example, those use to protect the eyes of a workman carrying out a welding process.

The invention claimed is:

1. An auto-darkening lens, comprising
   a controllable shutter having at least a relatively dark state and a relatively clear state,
   operating circuitry to operate the controllable shutter to such states,
   a sensor to sense incident electromagnetic energy, wherein the sensor is adapted to indicate to the operating circuitry the need for the operating circuitry to operate the controllable shutter to respective states, and
   a light guide to receive incident electromagnetic energy in proximity to the controllable shutter to guide such electromagnetic energy to the sensor,
   wherein the controllable shutter is mounted in a welding helmet.

2. An auto-darkening lens, comprising
   a controllable shutter having at least a relatively dark state and a relatively clear state,
   operating circuitry to operate the controllable shutter to such states,
   a sensor to sense incident electromagnetic energy, wherein the sensor is adapted to indicate to the operating circuitry the need for the operating circuitry to operate the controllable shutter to respective states, and
a light guide to receive incident electromagnetic energy in proximity to the controllable shutter to guide such electromagnetic energy to the sensor,
wherein the controllable shutter is a welding lens.

3. The lens of claim 2, said electromagnetic energy comprising light.

4. The lens of claim 2, said welding lens comprising a liquid crystal shutter.

5. The lens of claim 2, said operating circuitry including a power supply.

6. The lens of claim 2, said light guide comprising a light pipe.

7. The lens of claim 6, said light guide comprising a light inlet and a light outlet, the light inlet being in the area of the controllable shutter, and the light outlet being in the area to direct light to the sensor.

8. The lens of claim 7, said light guide comprising a solid material.

9. The lens of claim 7, said light guide comprising reflective surfaces in proximity to the light inlet and light outlet, and further comprising a light conductor for conducting light between the light inlet and the light outlet.

10. The lens of claim 7, said light guide comprising a solid light pipe.

11. The lens of claim 10, said solid light pipe comprising a plastic material.

12. The lens of claim 10, said solid light pipe comprising a polymer material.

13. The lens of claim 2, said light guide comprising a number of light directors.

14. The lens of claim 13, said sensor comprising a number of sensors corresponding to the number of light directors.

15. The lens of claim 2, said light guide comprising reflectors.

16. The lens of claim 2, said light guide comprising a prism.

17. The lens of claim 16, said prisms comprising a prism strip.

18. The lens of claim 17, said prism strip being at a side of the shutter.

19. The lens of claim 18, said prism strip including a prism strip at the bottom of the shutter.

20. The lens of claim 17, said prism strip comprising a prism strip at the bottom of the shutter.

21. The lens of claim 2, further comprising a housing supporting the controllable shutter, and wherein at least part of the sensor and operating circuitry are in the housing.

22. The lens of claim 21, wherein the light guide directs light into the housing to the sensor.

23. A control for an auto-darkening lens that has a controllable shutter providing a viewing window, comprising
a light responsive control to control a controllable shutter, and
a light director having a light inlet positionable in a viewing window area of a controllable shutter for directing light to the light responsive control,
said controllable shutter having a portion through which a user may view beyond the shutter, and wherein the light inlet is in the at least approximately in the area of said portion to receive incident light at least substantially representative of incident light on the shutter in a direction toward at least an eye of such user.

24. The control of claim 23, wherein the light responsive control comprises a photosensor and operating circuitry.

25. The control of claim 23, wherein the light director comprises a light conducting solid.

26. The control of claim 23, wherein the light director comprises a light pipe.

27. A control for an auto-darkening lens that has a controllable shutter providing a viewing window, comprising
a light responsive control to control a controllable shutter, and
a light director having a light inlet positionable in a viewing window area of a controllable shutter for directing light to the light responsive control,
wherein the light director comprises a reflecting surface, and
wherein the light director comprises a number of prisms.

28. The control of claim 27, wherein the prisms comprise a reflecting surface to reflect light to the light responsive control and a light transmitting surface.

29. A control for an auto-darkening lens that has a controllable shutter providing a viewing window, comprising
a light responsive control to control a controllable shutter, and
a light director having a light inlet positionable adjacent a viewing window area of a controllable shutter for directing light to the light responsive control,
said light director comprising a number of light directors, at least one light director positionable adjacent a viewing window at one side of such a viewing window area and at least one light director positionable adjacent the other side of such a viewing window.

30. An auto-darkening lens comprising a housing, a photosensor, a controllable shutter controllable in response to light sensed by the photosensor, and a light director for directing for the purpose of sensing by the photosensor light from an area at least one of in a viewing window of the controllable shutter or laterally adjacent the viewing window,
said light director comprising a light reflector,
said light reflector having a planar face.

31. An auto-darkening lens comprising a housing, a photosensor, a controllable shutter controllable in response to light sensed by the photosensor, and a light director for directing for the purpose of sensing by the photosensor light from an area at least one of in a viewing window of the controllable shutter or laterally adjacent the viewing window,
said light director comprising a light reflector,
said reflector having a convex curved reflective surface,
said convex curved reflective surface being positioned to receive incident light directed toward the viewing window over a relatively wide acceptance angle and to direct such light along a path toward the photosensor,
said light director comprising a light directing device and a collecting lens to tend to limit the amount of ambient light that is directed to the photosensor, and
said light directing device comprising a reflector and said collecting lens comprising a piano-convex lens.

32. An auto-darkening lens comprising a housing, a photosensor, a controllable shutter controllable in response to light sensed by the photosensor, and a light director for directing for sensing by the photosensor light from an area at least one of in a viewing window of the controllable shutter and laterally adjacent the viewing window, said light director comprising a prism on each lateral side of the viewing window, each of said prisms comprising a prism strip.

33. The lens of claim 32, wherein each prism strip includes a number of prisms.

34. The lens of claim 33, wherein a number of prisms in a prism strip include a light reflecting surface to reflect light that is incident thereon toward the sensor and a generally light transmitting surface for transmitting at least some light reflected from one toward the sensor.

35. A control for an auto-darkening lens comprising
a controllable shutter providing a viewing window of an eye protection device,
a light responsive control to control said controllable shutter, and
a light director having a light inlet positionable in a viewing window area of a controllable shutter for directing light to the light responsive control.

* * * * *

UNITED STATES PATENT AND TRADEMARK OFFICE
CERTIFICATE OF CORRECTION

| | |
|---|---|
| PATENT NO. | : 7,550,698 B2 |
| APPLICATION NO. | : 10/888197 |
| DATED | : June 23, 2009 |
| INVENTOR(S) | : John D. Fergason |

Page 1 of 1

It is certified that error appears in the above-identified patent and that said Letters Patent is hereby corrected as shown below:

Col. 14, Ln. 52 replace "piano" with --plano--.

Signed and Sealed this

Eleventh Day of August, 2009

David J. Kappos
*Director of the United States Patent and Trademark Office*